United States Patent
Guerrera et al.

(10) Patent No.: US 10,542,993 B2
(45) Date of Patent: Jan. 28, 2020

(54) ANVIL ASSEMBLY OF CIRCULAR STAPLING DEVICE INCLUDING ALIGNMENT SPLINES

(71) Applicant: Covidien LP, Mansfield, MA (US)

(72) Inventors: Joseph Guerrera, Watertown, CT (US); David Valentine, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 15/441,296

(22) Filed: Feb. 24, 2017

(65) Prior Publication Data

US 2018/0242973 A1    Aug. 30, 2018

(51) Int. Cl.
*A61B 17/115* (2006.01)
*A61B 17/072* (2006.01)

(52) U.S. Cl.
CPC .... *A61B 17/1155* (2013.01); *A61B 17/07207* (2013.01); *A61B 2017/07257* (2013.01); *A61B 2017/07271* (2013.01); *A61B 2017/1157* (2013.01)

(58) Field of Classification Search
CPC ...... A61B 17/1155; A61B 2017/00477; A61B 2017/07257
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

U.S. Appl. No. 15/441,994, filed Feb. 24, 2017, inventors: Joseph Guerrera and Patrick Mozdzierz.
European Search Report dated Jul. 13, 2018 in EP 18158432.

*Primary Examiner* — Gloria R Weeks
(74) *Attorney, Agent, or Firm* — Carter, DeLuca & Farrell LLP

(57) ABSTRACT

A tool assembly includes a cartridge assembly, a shell, and an anvil assembly. The shell houses the cartridge assembly and defines a passage. The shell includes alignment splines that are disposed within the passage and define channels between adjacent alignment splines. The anvil assembly includes an anvil and a center rod that extends from the anvil. The center rod defines a longitudinal axis and includes a first spline and second splines. The first spline includes a first leading facet that is configured to engage the alignment splines to clock the anvil assembly relative to the cartridge assembly. The second splines are radially spaced apart about the longitudinal axis. Each of the second splines includes a leading end that defines a plane that is substantially orthogonal to the longitudinal axis. The leading end is configured to crash with the alignments spines when the anvil assembly is misaligned with the cartridge assembly.

21 Claims, 12 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |

(56) References Cited

U.S. PATENT DOCUMENTS

| | | |
|---|---|---|
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0374670 A1 | 12/2016 | Fox et al. |
| 2016/0374672 A1 | 12/2016 | Bear et al. |

FOREIGN PATENT DOCUMENTS

| | | |
|---|---|---|
| CN | 101940485 A | 1/2011 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |
| WO | 2012072138 A1 | 6/2012 |

ANVIL ASSEMBLY OF CIRCULAR STAPLING DEVICE INCLUDING ALIGNMENT SPLINES

BACKGROUND

1. Technical Field

The present disclosure relates to surgical stapling devices and, more specifically, to structures and methods for aligning an anvil assembly with a cartridge assembly of a circular stapling device.

2. Discussion of Related Art

Circular stapling devices are employed by surgeons to apply one or more surgical fasteners, e.g., staples or two-part fasteners, to body tissue for the purpose of joining segments of body tissue together and/or for the creation of anastomoses. Circular stapling devices generally include an annular fastener cartridge assembly that supports a plurality of annular rows of fasteners, an annular anvil assembly operatively associated with the fastener cartridge assembly which provides a surface against which the fasteners are formed upon firing of the circular stapling device, and an annular blade for cutting tissue.

During a typical stapling procedure, the anvil assembly is separated from the stapling device and is positioned within one segment of body tissue. The stapling device is positioned in an adjacent segment of body tissue. The anvil assembly is then attached to the stapling device and the stapling device is actuated to approximate the anvil assembly with the cartridge assembly to clamp the segments of body tissue together. The stapling device is subsequently actuated to form the fasteners, and/or to sever tissue with the annular blade. It is important to accurately align the anvil assembly with the cartridge assembly to ensure the annular rows of fasteners are properly aligned with annular rows of staple pockets of the anvil assembly to facilitate proper formation of the fasteners upon actuation or firing of the stapling device.

Accordingly, there is a need for structures and methods for aligning the anvil assembly with the cartridge assembly to align the anvil assembly with the cartridge assembly to promote proper formation of fasteners.

SUMMARY

In an aspect of the present disclosure, a tool assembly includes a cartridge assembly, a shell, and an anvil assembly. The shell houses the cartridge assembly and defines a passage. The shell includes a plurality of alignment splines that are disposed within the passage with adjacent alignment splines defining channels therebetween. The anvil assembly includes an anvil and a center rod that extends from the anvil. The center rod defines a longitudinal axis and includes a first spline and a plurality of second splines. The first spline includes a first leading facet and a trailing end. The first leading facet is configured to engage at least one of the plurality of alignment splines to clock the anvil assembly relative to the cartridge assembly. The plurality of second splines are radially spaced apart about the longitudinal axis. Each of the second splines includes a leading end that defines a plane that is substantially orthogonal to the longitudinal axis. The leading end is configured to crash with a respective one of the plurality of alignments spines when the anvil assembly is misaligned with the cartridge assembly.

The anvil assembly may include a plurality of first splines that are radially spaced apart about the longitudinal axis.

In aspects, each of the channels is sized to receive at least one of the first or second splines to rotatably fix the anvil assembly relative to the shell. The first spline may include a second leading facet that forms a wedge with the first leading facet. The first and second leading facets may meet at a facet edge. The facet edge may be disposed along a centerline of a body of the first spline.

In some aspects, the first spline is configured to effect rotation of the anvil assembly in a single radial direction as the center rod is retracted through the passage. The first spline may have a body, a first side, a second side, the first leading facet, and a trailing end. The first leading facet may extend between the first and second sides. The first side may form a leading edge with the first leading facet and the second side may form a trailing edge with the first leading facet. The leading edge may be positioned proximal of the trailing edge. The single radial direction may be counterclockwise.

In certain aspects, the center rod includes a first alignment portion and a second alignment portion that are spaced apart from one another and define a gap therebetween. The first spline may be disposed on the first alignment portion and the plurality of second splines may be disposed about the second alignment portion. The first spline may be radially aligned with a respective one of the second splines. The gap may be in a range of about 0.25 inches to about 0.75 inches.

In particular aspects, the anvil is tiltable relative to the center rod between an orthogonal position and a fully tilted position. The gap may be sized such that the first spline is disposable within one of the channels of the shell when the anvil is in the fully tilted position.

In another aspect of the present disclosure, a circular stapling device includes a handle, an elongate body, and a tool assembly. The elongate body extends from the handle and the tool assembly is supported by the elongate body. The tool assembly includes a cartridge assembly, a shell, and an anvil assembly. The shell houses the cartridge assembly and defines a passage. The shell includes a plurality of alignment splines that are disposed within the passage such that adjacent alignment splines define channels therebetween. The anvil assembly includes an anvil and a center rod that extends from the anvil. The center rod defines a longitudinal rod axis and includes a first spline and a plurality of second splines. The first spline includes a first leading facet and a trailing end. The first leading facet is configured to engage at least one of the plurality of alignment splines to clock the anvil assembly with the cartridge assembly. The plurality of second splines are radially spaced apart about the rod axis. Each of the second splines includes a leading end that defines a plane substantially orthogonal to the rod axis. The leading end is configured to crash with a respective one of the plurality of alignment splines when the anvil assembly is misaligned with the cartridge assembly.

In aspects, the elongate body includes an anvil retainer and the center rod includes fingers that extend from the alignment portion away from the anvil. The fingers may be configured to releasably receive the anvil retainer. The anvil retainer may be configured to draw the center rod through the passage of the shell to approximate the anvil with the cartridge assembly. The fingers may be sized to pass through and rotate within the passage. A proximal portion of the fingers may form a collar. The center rod may include a first alignment portion that is adjacent the collar and a second alignment portion. The fingers may extend proximally from the second alignment portion towards the fingers. The first spline may be disposed on the first alignment portion and the plurality of second splines may be disposed about the second alignment portion. The first and second alignment portions may define a gap therebetween.

In another aspect of the present disclosure, a method of aligning an anvil assembly with a cartridge assembly of a circular stapling device includes drawing a center rod of the anvil assembly through a passage of a shell until a first spline that is disposed of the center rod engages an alignment mechanism of the shell, clocking the anvil assembly with the shell, and approximating the anvil assembly relative to the cartridge assembly. The shell houses the cartridge assembly. Clocking the anvil assembly with the shell includes continuing to draw the center rod through the passage such that the first spline cooperates with the alignment mechanism to rotate the anvil assembly about a longitudinal rod axis that is defined by the center rod. Approximating the anvil assembly relative to the cartridge assembly includes continuing to draw the center rod through the passage such that a plurality of second splines of the center rod, that are disposed distal to the first spline, cooperate with the alignment mechanism to rotatably secure the anvil assembly relative to the shell.

In aspects, clocking the anvil assembly with the shell includes engaging a first alignment spline of the alignment mechanism with the first spline to affect rotation of the anvil assembly in a known first direction about the rod axis.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
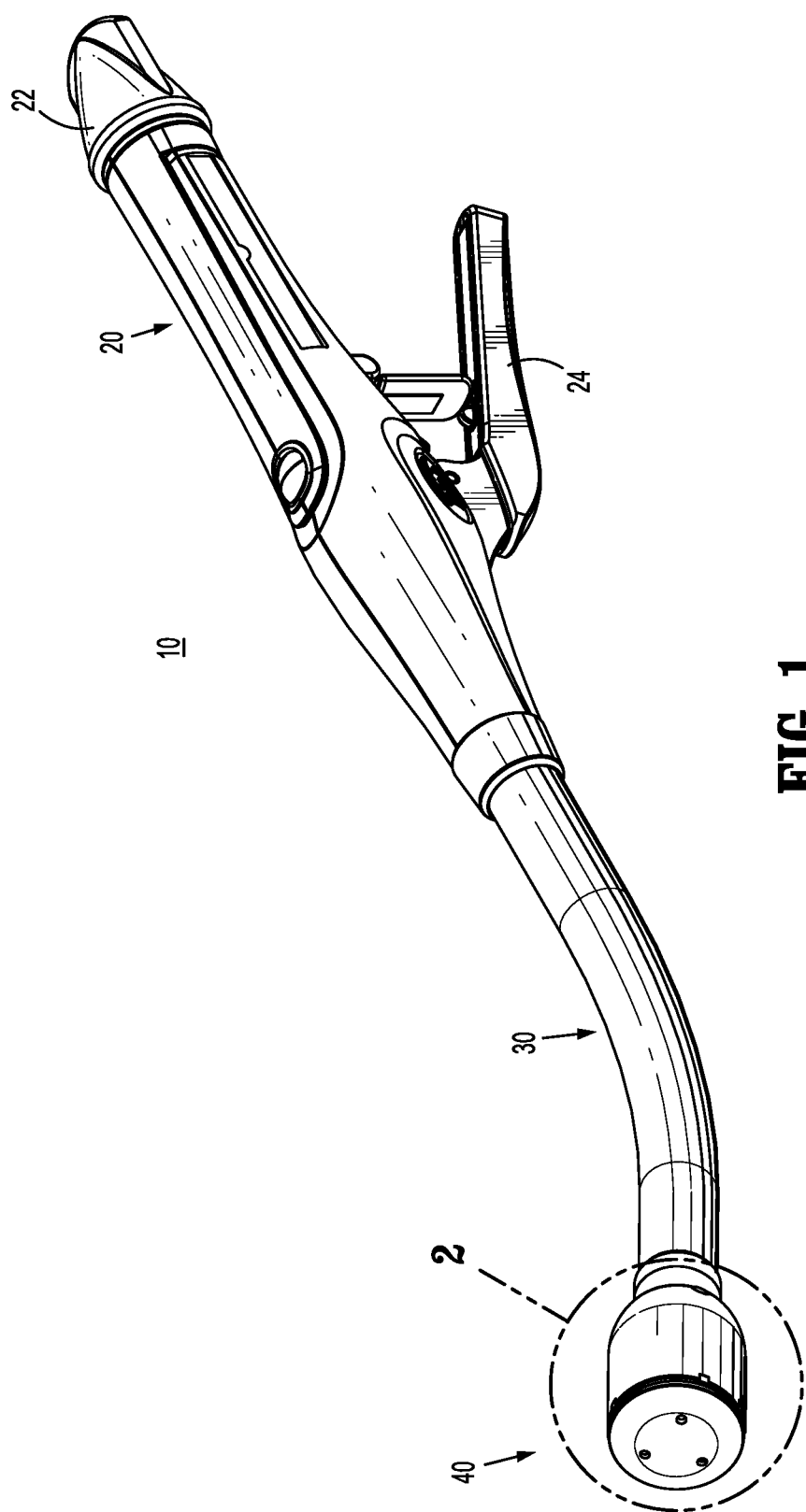
FIG. 1 is a perspective view of an exemplary circular stapling device including a tool assembly provided in accordance with the present disclosure.

This disclosure relates generally to a stapling device including a tool assembly having alignment features to promote proper formation of fasteners. The tool assembly includes a shell, a cartridge assembly, and an anvil assembly. The cartridge assembly is releasably housed within the shell and the anvil assembly is movably supported on the stapling device in relation to the cartridge assembly. The anvil assembly includes a center rod having locating splines and one or more tombstone splines. The shell defines a passage for receiving the center rod of the anvil assembly and includes alignment splines that are disposed within the passage. The locating splines are positioned to be engaged with and/or received between adjacent alignment splines of the shell to clock the anvil assembly relative to the shell such that the anvil assembly is aligned with the cartridge assembly to properly form fasteners upon actuation of the tool assembly. The tombstone splines are received between the adjacent alignment splines subsequent to the locating splines being received between adjacent alignment splines to rotatably fix the anvil assembly in relation to the shell. In embodiments, the tombstone splines are configured to crash into the alignment splines to enhance detection of misalignment of the anvil assembly and the shell assembly.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to that portion of the device or component thereof that is closest to the clinician and the term "distal" refers to that portion of the device or component thereof that is farthest from the clinician. In addition, as used in this description, the term "clock" refers to rotationally aligning or orientating two components with one another.

Referring initially to FIG. 1, a circular stapling device is disclosed herein and is generally designated as 10. In embodiments, the circular stapling device 10 is adapted for reuse and, in certain embodiments; the circular stapling device 10 is adapted for a single use and can be disposable.

The circular stapling device 10 includes a handle assembly 20, an elongate body 30, and a tool assembly 40. The tool assembly 40 can be provided as a removable and replaceable assembly that is secured to a distal portion of the elongate body 30. The handle assembly 20 includes a rotatable advancing member 22 and a pivotable trigger member 24 that are operatively coupled to mechanisms supported within the elongate body 30 to effectuate approximation and firing of the surgical stapling device 10. The elongate body 30 extends distally from a distal portion of the handle assembly 20 to a proximal portion of the tool assembly 40 so that the elongate body 30 is disposed between the handle assembly 20 and the tool assembly 40. In some embodiments, the elongate body 30 has a linear shape along the length of the elongate body 30, and in certain embodiments, the elongate body 30 has a curved shape along the length of the elongate body 30.

Figure 2:
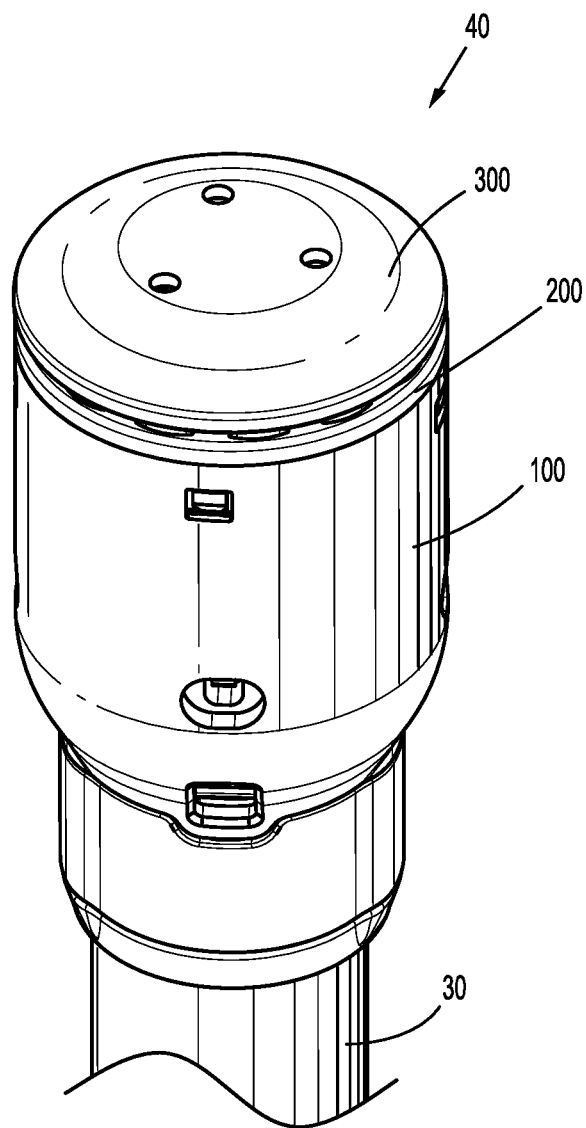
FIG. 2 is an enlarged view of the indicated area of detail of FIG. 1 illustrating the tool assembly in a clamped configuration.
Figure 3:
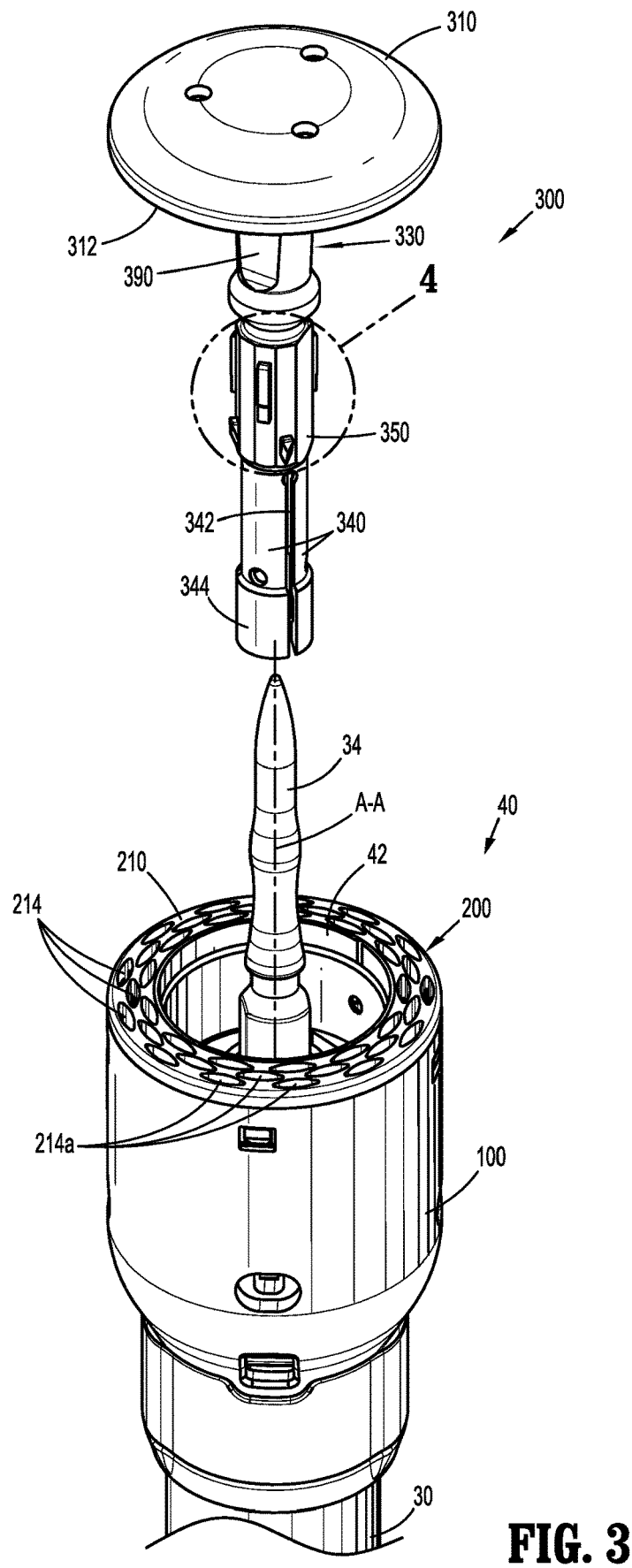
FIG. 3 is perspective view of the tool assembly with an anvil assembly separated from a shell.

With reference to FIGS. 2 and 3, the tool assembly 40 includes a shell 100, a cartridge assembly 200, and an anvil assembly 300. The shell 100 houses a plurality of additional components that do not form part of this disclosure and are not shown or described further herein. In embodiments, the cartridge assembly 200 and/or the anvil assembly 300 may be replaced and the circular stapling device 10 may be reused. In embodiments, the tool assembly 40 includes a knife assembly with a substantially annular knife 42 adapted to cut tissue.

For a detailed discussion of the construction and operation of exemplary circular stapling devices reference may be made to U.S. Pat. Nos. 5,915,616; 8,789,737; and 8,806,973; the entire contents of each of which are incorporated herein by reference.

The shell 100 houses the cartridge assembly 200 and receives a portion of the anvil assembly 300. The cartridge assembly 200 includes a tissue contacting surface 210 that defines a plurality of fastener retention slots 214 each including an opening 214a. The openings 214a are arranged in coaxial annular rings positioned about the tissue contacting surface 210. As shown, the tissue contacting surface 210 defines three annular rings of openings 214a; however, it is contemplated that the tissue contacting surface 210 may include more or less annular rings of openings 214a, e.g., 2, 5, 6, etc. The cartridge assembly 200 further includes a fastener or a first part of a fastener (not shown) disposed within each of the retention slots 214.

Referring to FIG. 3, the anvil assembly 300 includes an anvil 310 and a center rod 330. The anvil 310 includes a tissue contacting surface 312 that defines a plurality of pockets (not shown) that align with the openings 214a of the cartridge assembly 200 to form fasteners upon actuation of the trigger 24 (FIG. 1). Alternatively, each of the pockets can include a second part of a two-part fastener that engages a first part of the two-part fastener disposed within one of the retention slots 214 as known in the art.

The center rod 330 is pivotally coupled to the anvil 310 such that the anvil 310 can tilt relative to the center rod 330. Alternatively, the center rod 330 may be fixedly coupled to the anvil 310 such that the center rod 330 extends substantially orthogonally away from the tissue contacting surface 312 of the anvil 310. For example, the center rod 330 may define an angle in a range of about 80° to about 100° with the tissue contacting surface 312 of the anvil 310. The center rod 330 extends proximally from the anvil 310 and is configured to pass through the shell 100 and couple to an anvil retainer, e.g., a trocar 34, of the elongate body 30 (FIG. 1). The trocar 34 is configured to draw the anvil 310 to an approximated or clamped configuration (FIG. 2) in response to rotation of the rotatable advancing member 22 (FIG. 1). In the clamped configuration, the tissue contacting surface 312 of the anvil 310 is approximated with the tissue contacting surface 210 of the cartridge 200 such that fasteners are formable through tissue clamped between the tissue contacting surfaces 210, 312 as shown in FIG. 2. In some embodiments, the anvil retainer of the elongate body 30 includes fingers, similar to fingers 340, and the center rod 330 includes a trocar, similar to trocar 34, that is received by the fingers of the elongate body 30 to couple the anvil assembly 300 to the elongate body 30.

Figure 10:
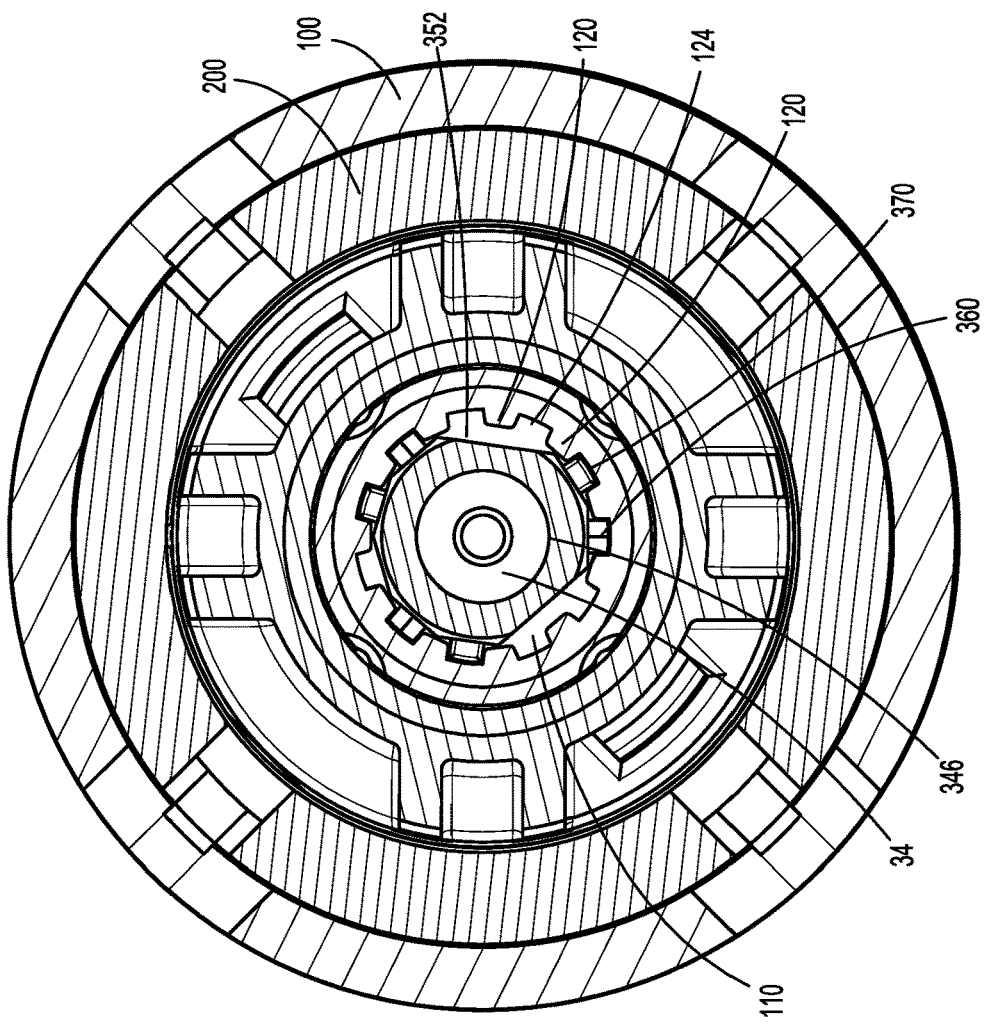
FIG. 10 is a cross-sectional view taken along section line 10-10 of FIG. 9.
Figure 9:
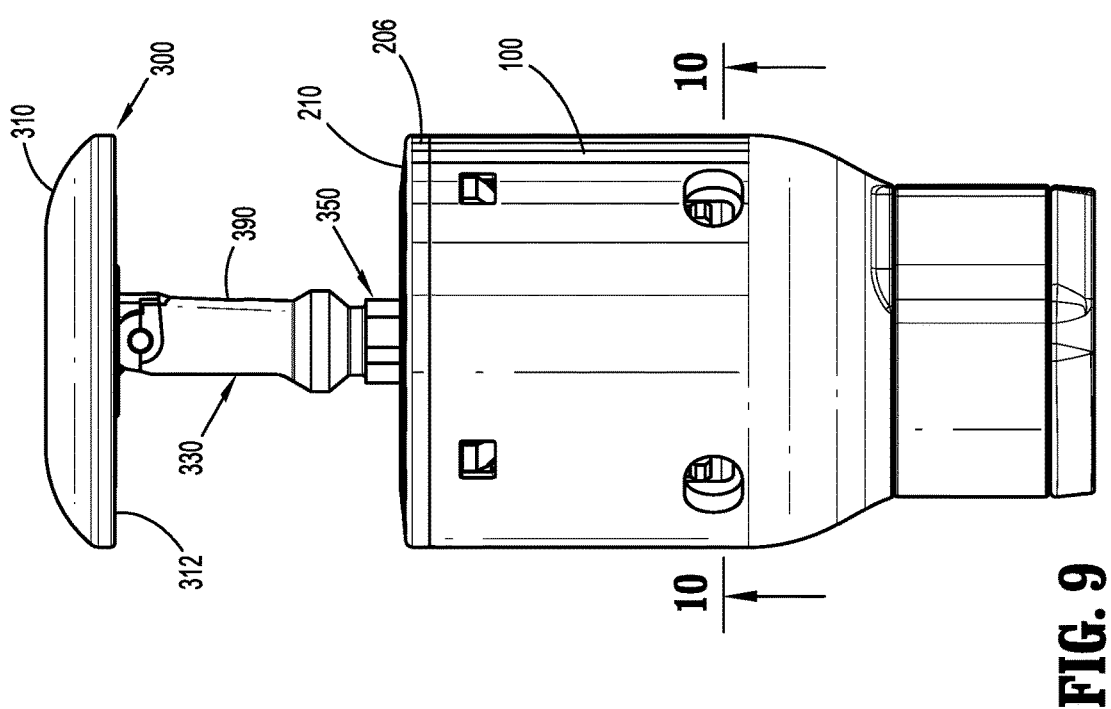
FIG. 9 is a side view of the tool assembly of FIG. 3 with a center rod of the anvil assembly partially received within the shell.

The center rod 330 defines a longitudinal axis A-A (FIG. 3) of the anvil assembly 300 and includes fingers 340, an alignment portion 350, and a distal shaft 390. The alignment portion 350 is positioned between the distal shaft 390, which couples to the anvil 310, and the fingers 340. The fingers 340 define a cavity 346 (FIG. 10) that releasably receives the trocar 34. The fingers 340 each extend proximally from the alignment portion 350 to substantially form a cylinder with slits 342 defined between each of the fingers 340. The slits 342 permit the fingers 340 to expand outward to receive the trocar 34 within the cavity 346. A proximal portion of the fingers 340 includes a retention collar 344 which is configured to be received within the shell 100 when the trocar 34 is received within the fingers 34 to prevent the fingers 340 from expanding. By preventing expansion of the fingers 340, separation of the anvil assembly 300 from the trocar 34 during approximation and firing is prevented. The distal shaft 390 is substantially cylindrical in shape and is positioned along the longitudinal axis A-A.

Figure 5:
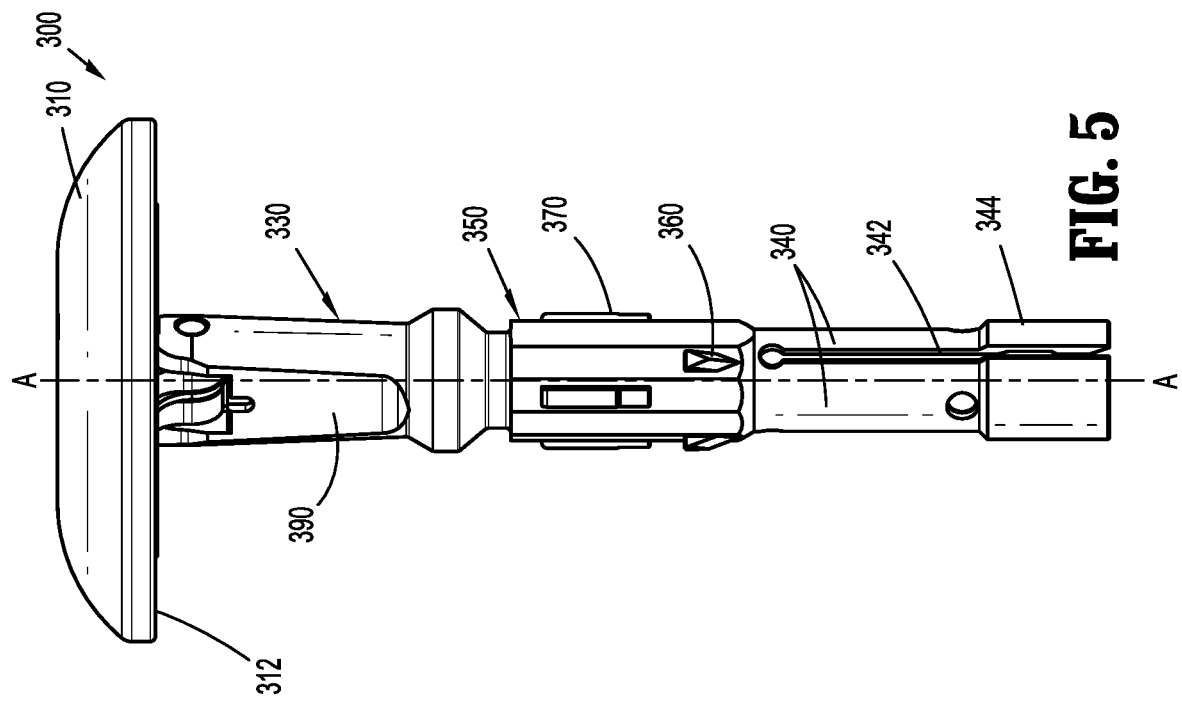
FIG. 5 is a side view of the anvil assembly of FIG. 3.
Figure 4:
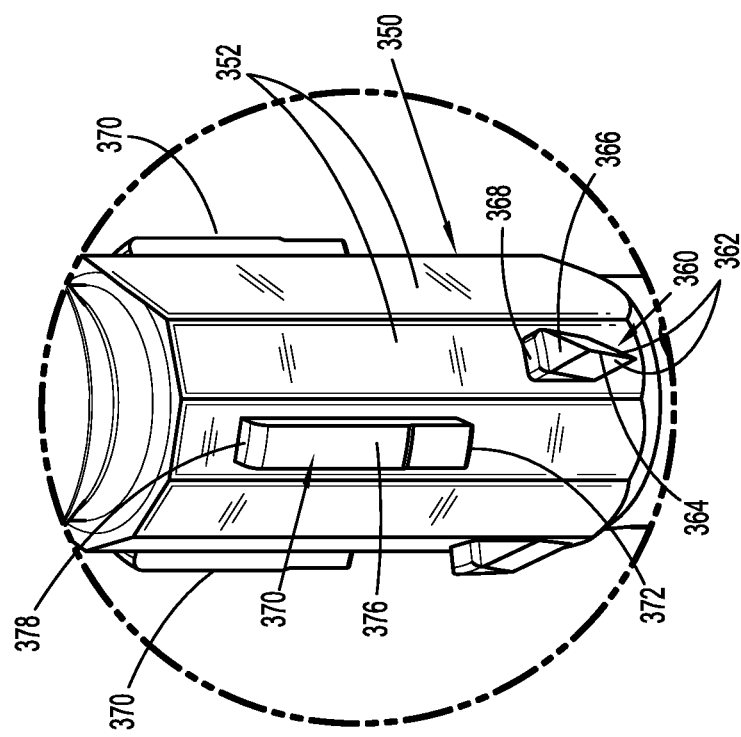
FIG. 4 is an enlarged view of the indicated area of detail of FIG. 3.

Referring to FIGS. 4 and 5, the alignment portion 350 of the anvil assembly 300 defines a plurality of faces 352 such that the alignment portion 350 has a polygonal cross-section in a plane orthogonal to the longitudinal axis A-A. As shown, the alignment portion 350 has 9 faces 352; however, the alignment portion 350 can have about 3 to about 18 faces. The alignment portion 350 includes first or locating splines 360 and second or tombstone splines 370 which are each disposed on a respective face 352 of the plurality of faces 352 of the alignment portion 350 and are radially spaced apart from one another. In embodiments, the width of the faces 352 may vary about the alignment portion 350. In embodiments, the locating and tombstone splines 360, 370 are disposed on faces 352 that have a smaller width than the width of the faces 352 without a locating or tombstone spline 360, 370. This configuration may provide additional clearance for the alignment portion 350 within the shell 100 (FIG. 8) as detailed below. It is contemplated that each of the faces 352 of the alignment portion 350 may have an equal width and further that only some or all of the faces 352 may support a spline 360, 370. As shown, the alignment portion 350 includes multiple locating splines 360; however, the alignment portion 350 may include a single locating spline 360. It will be appreciated that the alignment portion 350 may include any number of locating splines 360 up to a number of locating splines 360 equal to the number of tombstone splines 370.

Each of the locating splines 360 has a pair of leading facets 362 forming a wedge and a body 366 extending distally from the leading facets 362 to a trailing end 368 of the body 366 in a direction parallel to the longitudinal axis A-A. The leading facets 362 meet at a facet edge 364 that is positioned substantially along a centerline of the body 366. By positioning the facet edge 364 substantially along the centerline of the body 366, the locating spline 360 is configured to rotate the center rod 330 in either a clockwise or a counter-clockwise direction about the longitudinal axis A-A, as viewed from a proximal end of the center rod 330, as the center rod 330 passes through the shell 100 (FIG. 6) as detailed below.

Figure 7:
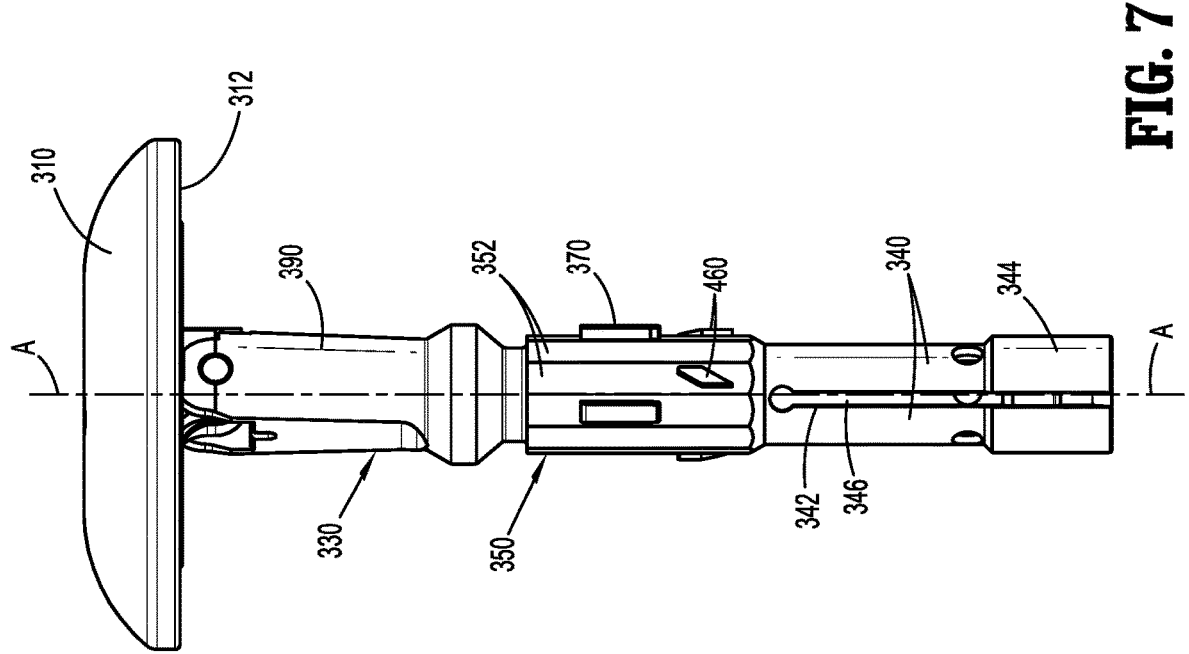
FIG. 7 is a side view of the anvil assembly of FIG. 6.
Figure 6:
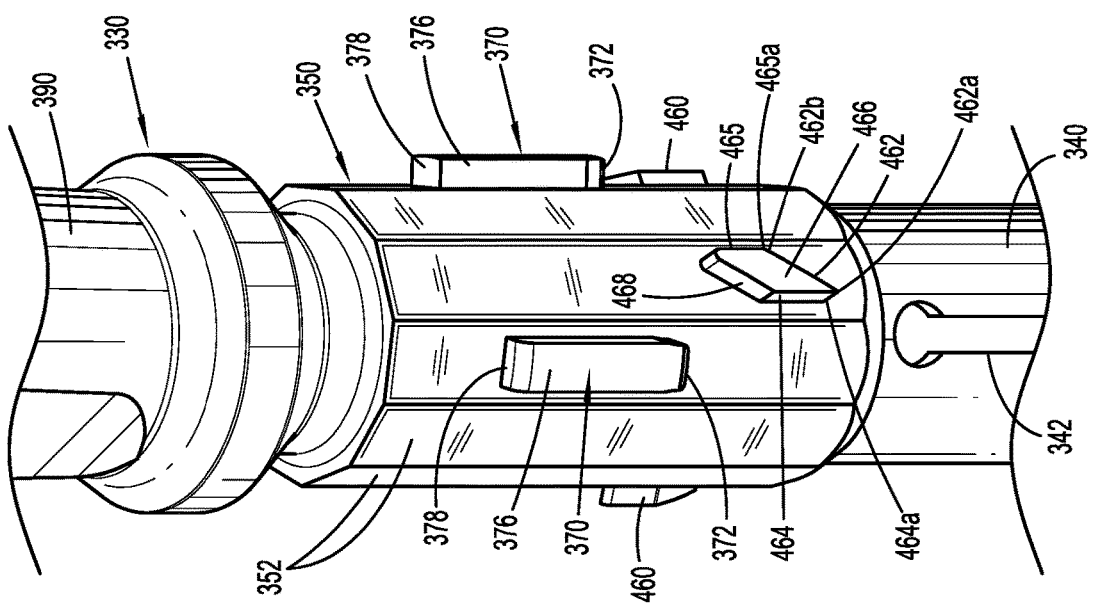
FIG. 6 is perspective view of a portion of another anvil assembly illustrating a directional locating spline provided in accordance with the present disclosure.
Figure 8:
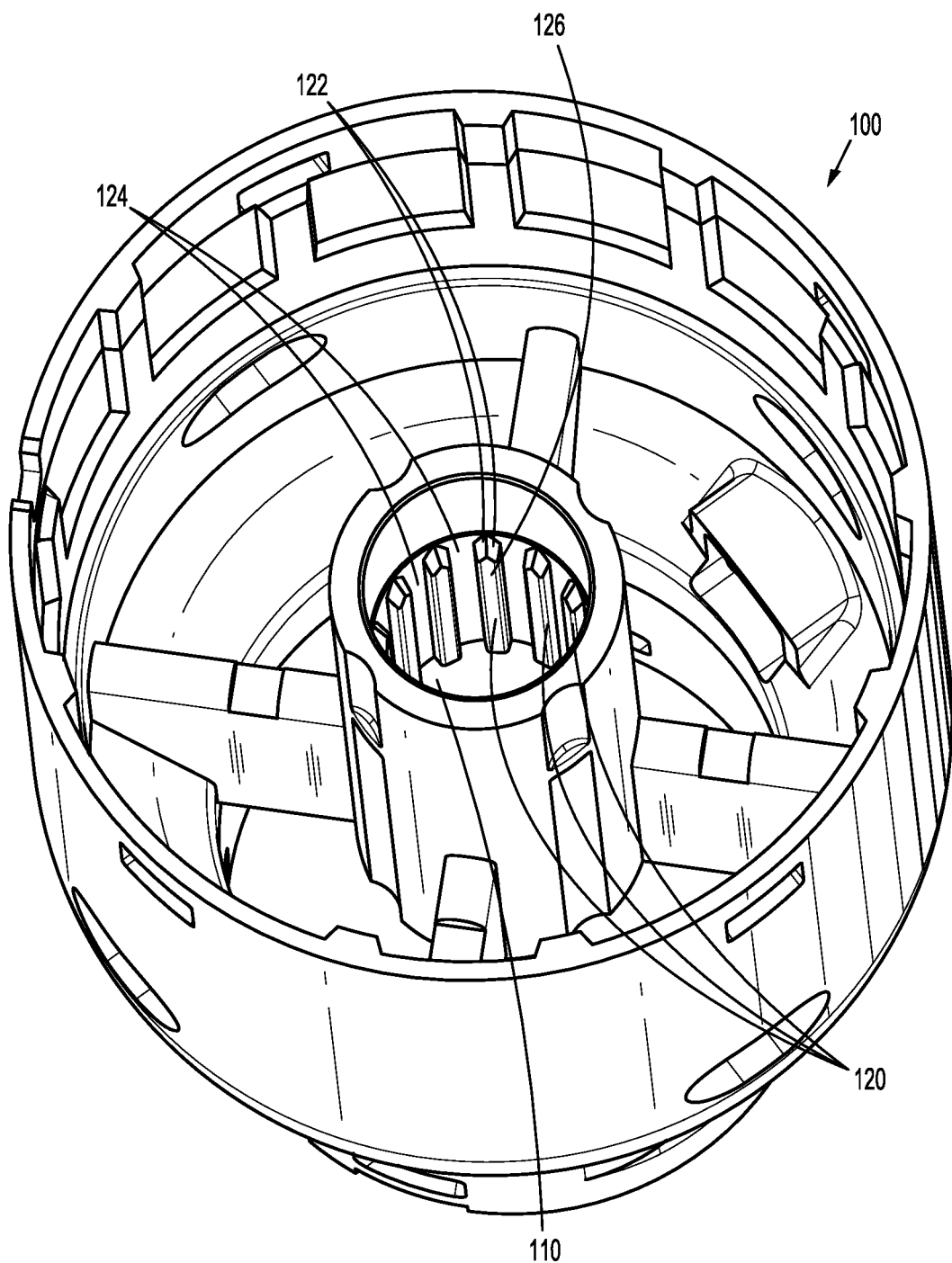
FIG. 8 is an end, perspective view of the shell of FIG. 3 with a cartridge assembly removed.

Referring to FIGS. 6 and 7, in an alternate embodiment, the alignment portion 350 can include directional locating splines 460. Each of the directional locating splines 460 has a body 466 that includes a leading facet 462, a first side 464, a second side 465, and a trailing facet or end 468. Each of the first and second sides 464, 465 extend in a direction parallel to the longitudinal axis A-A of the center rod 330 and are sized substantially equal to one another. The first side 464 has a leading end 464a that is positioned proximal of a leading end 465a of the second side 465. The leading facet 462 forms a leading edge 462a with the leading end 464a of the first side 464 and a trailing edge 462b with the leading end 465a of the second side 465. By orientating the leading facet 462 as shown in FIGS. 6 and 7, the locating spline 460 is configured to rotate the center rod 330 in a counter-clockwise direction about the longitudinal axis A-A as the center rod 330 passes through the shell 100 (FIG. 8) as detailed below. It is contemplated that the leading facet 462 can be oriented to rotate the center rod 330 in a clockwise direction about the longitudinal axis A-A as the center rod 330 passes through the shell 100 (FIG. 8). The directional locating splines 460 allow for rotation of the anvil assembly 300 in a known direction as the center rod 330 passes through the shell 100.

Referring to FIGS. 4 and 6, each of the tombstone splines 370 has a leading end 372, a body 376, and a trailing end 378. The leading end 372 defines a plane orthogonal to the longitudinal axis A-A. The body 376 extends distally from the leading end 372 to the trailing end 378 in a direction parallel to the longitudinal axis A-A. The leading ends 372 of the tombstone splines 370 are positioned distal to the trailing ends 368, 468 of the locating splines 360, 460.

With reference to FIG. 8, the shell 100 defines a central passage 110 including a plurality of alignment splines 120 extending into the passage 110. The passage 110 is sized to permit the fingers 340 of the anvil assembly 300 to pass through the passage 110. Each of the alignment splines 120 is spaced apart from adjacent splines 120 to define channels 124 therebetween. Each alignment spline 120 includes a pair of alignment surfaces 122 that form a wedge and a body 126 extending proximally away from the alignment surfaces 122.

The channels 124 are sized and dimensioned to receive the body 366 of the locating splines 360 and the bodies 376 of the tombstone splines 370 to clock or align the pockets of the anvil assembly 310 with the fastener retention slots 214 of the cartridge assembly 200 and, thereafter to fix the orientation the anvil assembly 300 relative to the shell 100 and the cartridge assembly 200. When the locating and tombstone splines 360, 370 are received within channels 124 of the shell 100, the fastener retention slots 214 (FIG. 3) of the cartridge assembly 200 are aligned with the pockets of the anvil 310 to promote proper fastener formation. It will be appreciated that the locating splines 460 function in a similar manner to the locating splines 360 to align the tombstone splines 370 with the channels 124 of the shell 100.

Figure 11:
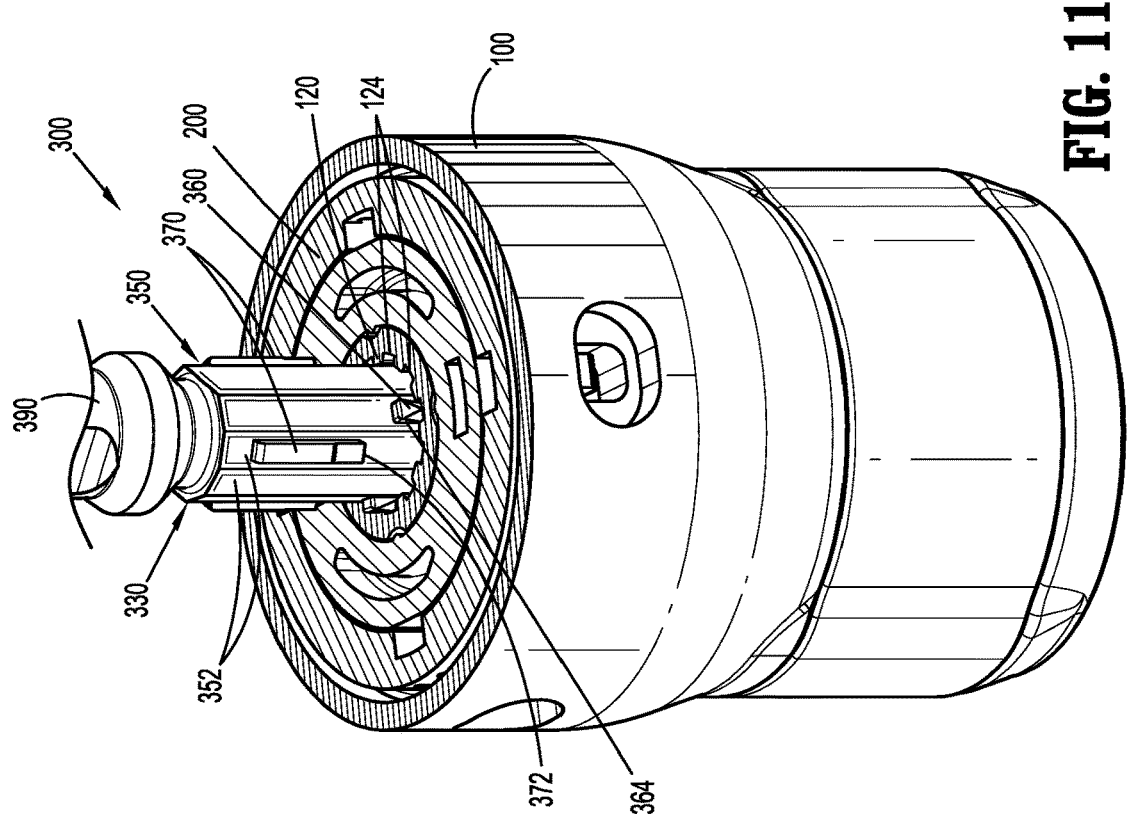
FIG. 11 is a perspective, cut-away, cross-sectional view of the tool assembly of FIG. 9 illustrating locating splines of the anvil assembly as the locating splines are engage and are received between adjacent alignment splines of the shell.

Referring to FIGS. 9-12, as the center rod 330 of the anvil assembly 300 is drawn through the passage 110 of the shell 100, the fingers 340 pass through the passage 110 of the shell 100. After the fingers 340 pass beyond the alignment splines 120 within the passage 110, the leading facets 364 of the locating splines 360 engage the alignment surfaces 122 of the alignment splines 120 if the bodies 366 are misaligned with the channels 124 defined between the alignment splines 120. Engagement between the leading facets 364 and the alignment surfaces 122 will effect rotation of the anvil assembly 300 about the center rod 330 to guide the bodies 366 of the locating splines 360 into respective channels 124 as shown in FIG. 11. As the leading facets 364 engage the alignment surfaces 122, the anvil assembly 300 rotates about the longitudinal axis A-A to clock the anvil assembly 300 relative to the shell 100. As the anvil assembly 300 rotates to position the locating splines 360 into the channels 124, the bodies 376 of the tombstone splines 370 are orientated to pass through respective channels 124 between adjacent alignment splines 120. When the bodies 366, 376 of the locating splines 360 and the tombstone splines 370 are positioned within respective channels 124, the pockets of the anvil 310 (not shown) are aligned with the fastener retention slots 214 (FIG. 3) of the cartridge 200 such that fasteners will be properly formed when the fasteners are received and deformed within the pockets of the anvil 310.

With particular reference to FIG. 11, the leading facets 364 of the locating splines 360 are positioned proximal to the leading ends 372 of the tombstone splines 370 such that the locating splines 360 engage the alignment splines 120 before the tombstone splines 370 to clock the anvil assembly 300 to the shell 100. By positioning the leading portion 362 (FIG. 4) of the locating splines 360 proximally of the leading ends 372 of the tombstone splines 370, "crashing" of splines, caused by simultaneous engagement of multiple splines of the anvil assembly 310 with alignment splines 120 of the shell 100, is reduced or eliminated. As used herein, "crashing" refers to a force experience as a result of abutment of two surfaces that stops or reduces movement of one of the surfaces in a particular direction. "Crashing" can also mean the engagement of surfaces, and/or some sort of collision. The shape of the locating splines 360 reduce engagement forces between the locating splines 360 and the alignment splines 120 as the anvil assembly 330 is clocked relative to the shell 100.

Figure 12:
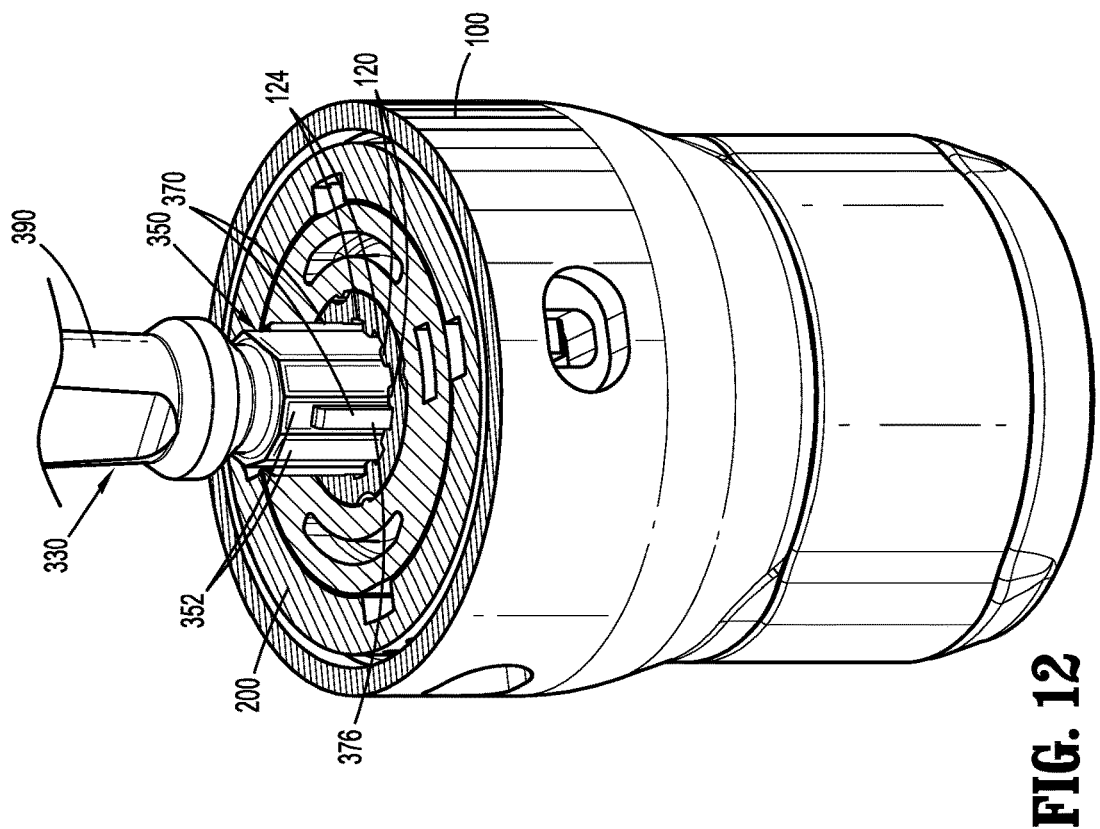
FIG. 12 is a perspective, cut-away, cross-sectional view of the tool assembly of FIG. 11 with the anvil assembly drawn into the shell with the locating splines and tombstone splines received between the adjacent alignment splines of the shell.

Referring to FIG. 12, as the center rod 330 continues to be drawn through the passage 110 of the shell 100, the bodies 366 (FIG. 4) of the locating splines 360 are each received within a respective one of the channels 124 defined between adjacent alignment splines 120. Thereafter, the leading end 372 (FIG. 11) of each of the tombstone splines 370 enters a respective one of the channels 124 to align and rotatably fix the anvil assembly 300 with the shell 100. As the leading ends 372 of the tombstone splines 370 enter the respective channels 124, the orientation or clocking of the anvil assembly 300 relative to the shell 100 may be finely adjusted. When the center rod 330 is drawn through the passage 110 to move the anvil assembly 300 to the clamped position (FIG. 2), the bodies 366, 376 (FIG. 4) are each disposed within a respective channel 124 to align the pockets of the anvil assembly 330 with the fastener retention slots 214 (FIG. 3) of the cartridge assembly 200 and to rotationally fix the anvil assembly 330 relative to the cartridge assembly 200. It will be appreciated that when the bodies 376 of the tombstone splines 370 are received between adjacent alignment splines 120, the area of engagement between the tombstone splines 370 and the alignment splines 120 to resist rotation of the center rod 330 is increased to increase resistance to relative rotation between the anvil assembly 300 and the shell 100. Further, it will be appreciated that as the number of tombstone splines 370 increases the area of engagement between the anvil assembly 300 and the shell 100 can be increased to increase resistance to relative rotation between the anvil assembly 300 and the shell 100.

The leading ends 372 of the tombstone splines 370 define planes orthogonal to the longitudinal axis A-A to "crash" into a respective alignment spline 120 to allow for easy detection of spline crash. Detecting spline crash at the initial engagement of the tombstone splines 370 and the alignment splines 120 provides an indication of misalignment between the anvil assembly 300 and the shell 100 before fastener formation. The misalignment of the tombstone splines 370 and the alignment splines 120 may occur from torque applied to the anvil 310 (FIG. 8) engaging tissue as the tissue is compressed between the anvil 310 and the cartridge 200 (FIG. 8). These high crash forces occur before the highest compression forces of tissue between the tissue contacting surfaces 210, 312 (FIG. 4) occur as the anvil assembly 300 is drawn towards the cartridge assembly 200 to reduce increased trauma to tissue from multiple compressions. In addition, these high crash forces reduce the likelihood of false detection of spline crash during retraction of the anvil assembly 300 which may increase the confidence of a clinician that the pockets of the anvil 310 are properly aligned the fastener retention slots 214 (FIG. 3) of the cartridge 200 such that fasteners will be properly formed when the fasteners are ejected or fired from the cartridge 200 upon actuation of the trigger 24 (FIG. 1). It is contemplated that spline crash between the tombstone splines 370 and the alignment splines 120 may also be used to detect an anvil mismatch between the anvil 310 and a particular shell 100 or cartridge assembly 200. When spline crash is detected, retraction of the anvil assembly 300 is reversed and then restarted such that the locating splines 360 are allowed to clock the anvil assembly 300 with the shell 100. Alternatively, when anvil mismatch is suspected, the anvil 300 can be removed and a suitable anvil 300 be selected to match the cartridge assembly 200 and/or shell 100. The term "anvil mismatch" as used herein is an anvil having pockets that do not correspond to fasteners of a cartridge assembly housed within the shell 100.

It will be appreciated that the function of locating splines 460 is substantially similar to the function of locating splines 360 as detailed above, as such only the differences will be detailed for brevity. Locating splines 460 affect rotation of the anvil assembly 330 in a known direction such that as the anvil assembly 300 is retracted towards the cartridge assembly 200, a clinician can observe rotation of the anvil 310 in the known direction. When rotation of the anvil 310 in the known direction stops, an indication is provided to the clinician that the pockets of the anvil 310 are aligned with the fastener retention slots 214 (FIG. 3) of the cartridge 200 such that fasteners will be properly formed when the fasteners are ejected or fired from the cartridge 200.

Referring to FIGS. 13-16, another anvil assembly 1300 is provided in accordance with the present disclosure. The anvil assembly 1300 is similar and functions in a similar manner to the anvil assembly 300 detailed above with like elements represented with a similar label with a "1" preceding the previous label. As such, only the differences between anvil assembly 1300 and anvil assembly 300 will be detailed herein for reasons of brevity.

Figure 13:
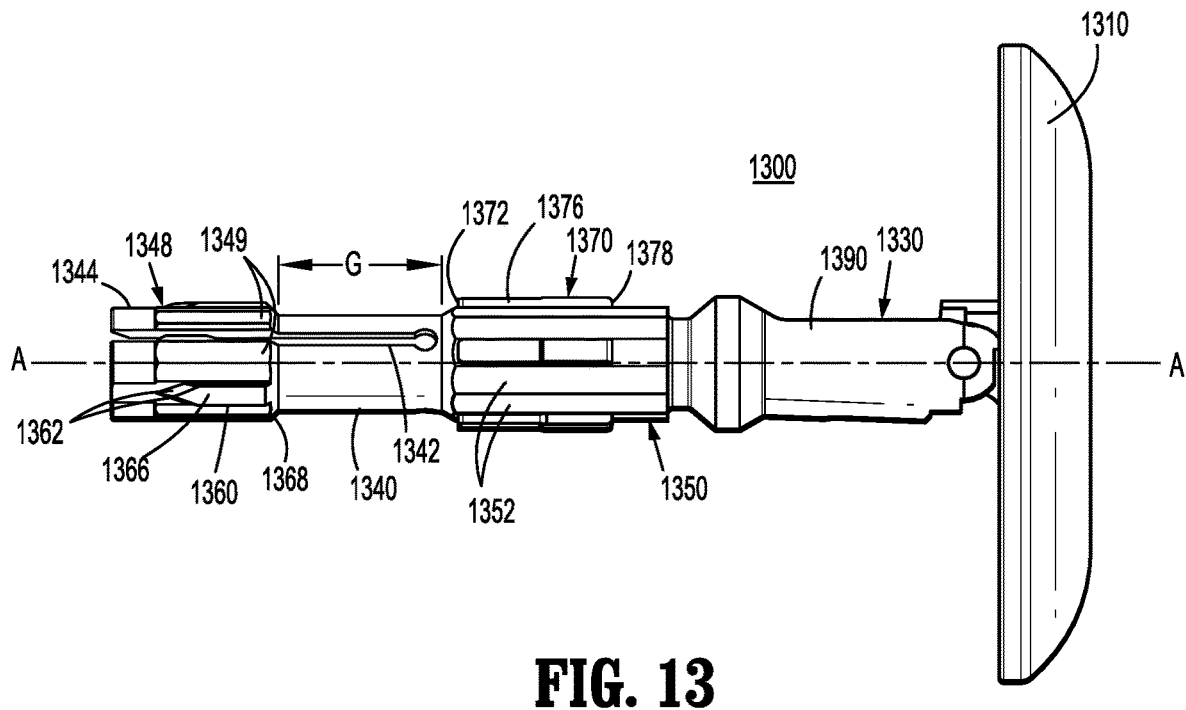
FIG. 13 is a side view of another anvil assembly provided in accordance with the present disclosure.

Initially referring to FIG. 13, the anvil assembly 1300 includes an anvil 1310 and a center rod 1330 extending from the anvil 1310. The center rod 1330 includes an engagement portion, e.g., resilient fingers 1340, a proximal alignment portion 1348, a distal alignment portion 1350, and a distal portion 1390. The distal portion 1390 at the center rod 1330 is pivotally coupled to the anvil 1310 by a pivot member 1392. The fingers 1340 extend proximally from the distal alignment portion 1350 and include a collar 1344.

The proximal alignment portion 1348 is disposed about a portion of the fingers 1340 distal of the collar 1344. In embodiments, the proximal alignment portion 1348 may be disposed at least partially on the collar 1340. The proximal alignment portion 1348 includes faces 1349 forming a polygonal shape in a plane orthogonal to the longitudinal axis A-A of the center rod 1330 and one or more locating splines 1360 that each extend from one of the faces 1349. The locating splines 1360 can be similar to the locating splines 360 or directional locating splines 460 detailed above and include leading facets 1364 that engage the alignment splines 120 of the shell (FIG. 15) to clock the anvil assembly 1300 about the longitudinal axis A-A in a manner similar to the locating splines 360, 460 detailed above.

The distal alignment portion 1350 is spaced apart from the proximal alignment portion 1348 such that a portion of the fingers 1340 is positioned between the proximal and distal alignment portions 1348, 1350 to define a gap "G" therebetween. The gap "G" defines a length in a range of about 0.25 inches to about 0.75 inches, e.g., about 0.5 inches. It is envisioned that for particular applications the gap "G" may be greater than 0.75 inches.

Figure 14:
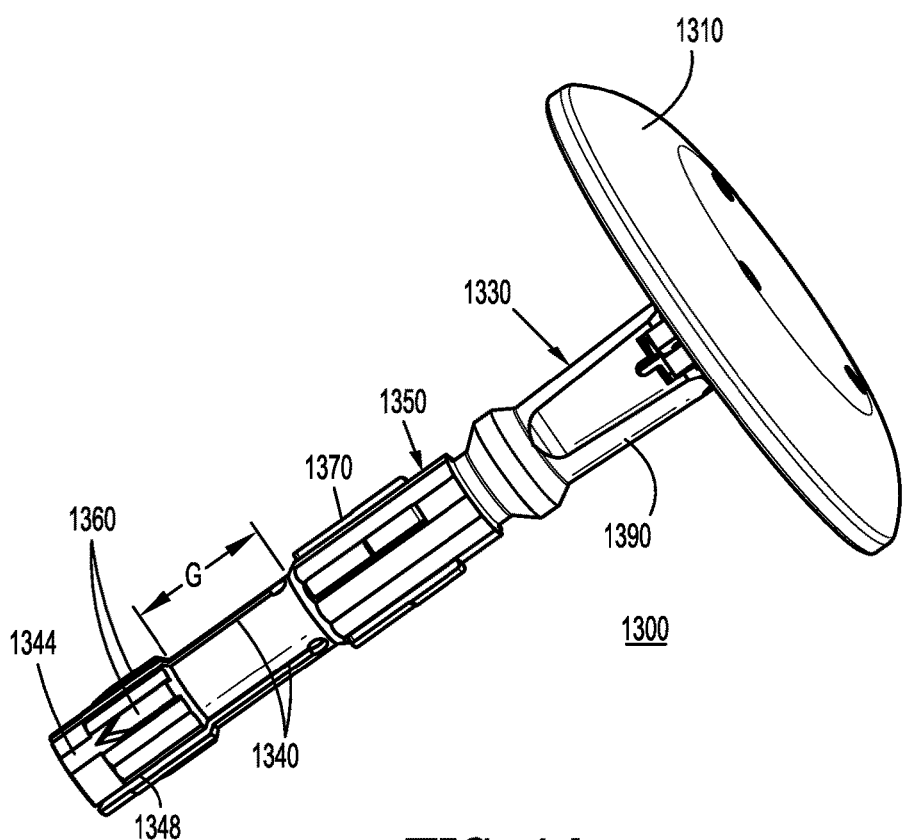
FIG. 14 is a side view of yet another anvil assembly provided in accordance with the present disclosure.

The distal alignment portion 1350 includes tombstone splines 1370 which are substantially similar to the tombstone splines 370 detailed above. As shown in FIG. 13, each of the tombstone splines 1370 are radially offset from the locating splines 1360 in a similar manner as detailed above with respect to locating splines 360 and tombstone splines 370 detailed above. In contrast and as shown in FIG. 14, each of the tombstone splines 1370 may be radially aligned with a respective one of the locating splines 1360 such that each tombstone spline 1370 will be disposed within the same channel 124 (FIG. 15) as the respective one of the locating splines 1360.

Figure 15:
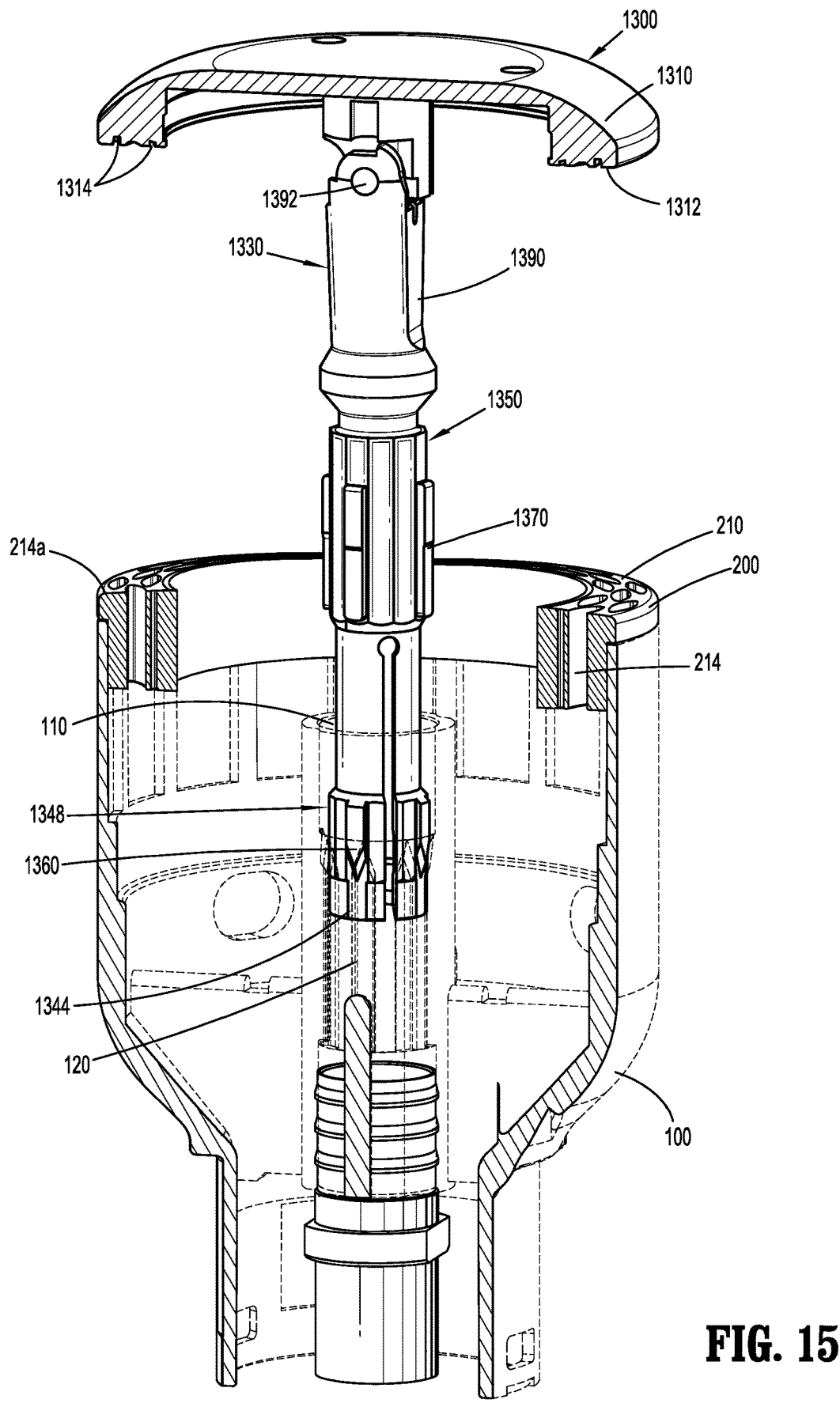
FIG. 15 is a cross-sectional view of a tool assembly in accordance with the present disclosure with locating splines of the anvil assembly of FIG. 13 received between adjacent alignment splines of the shell.
Figure 16:
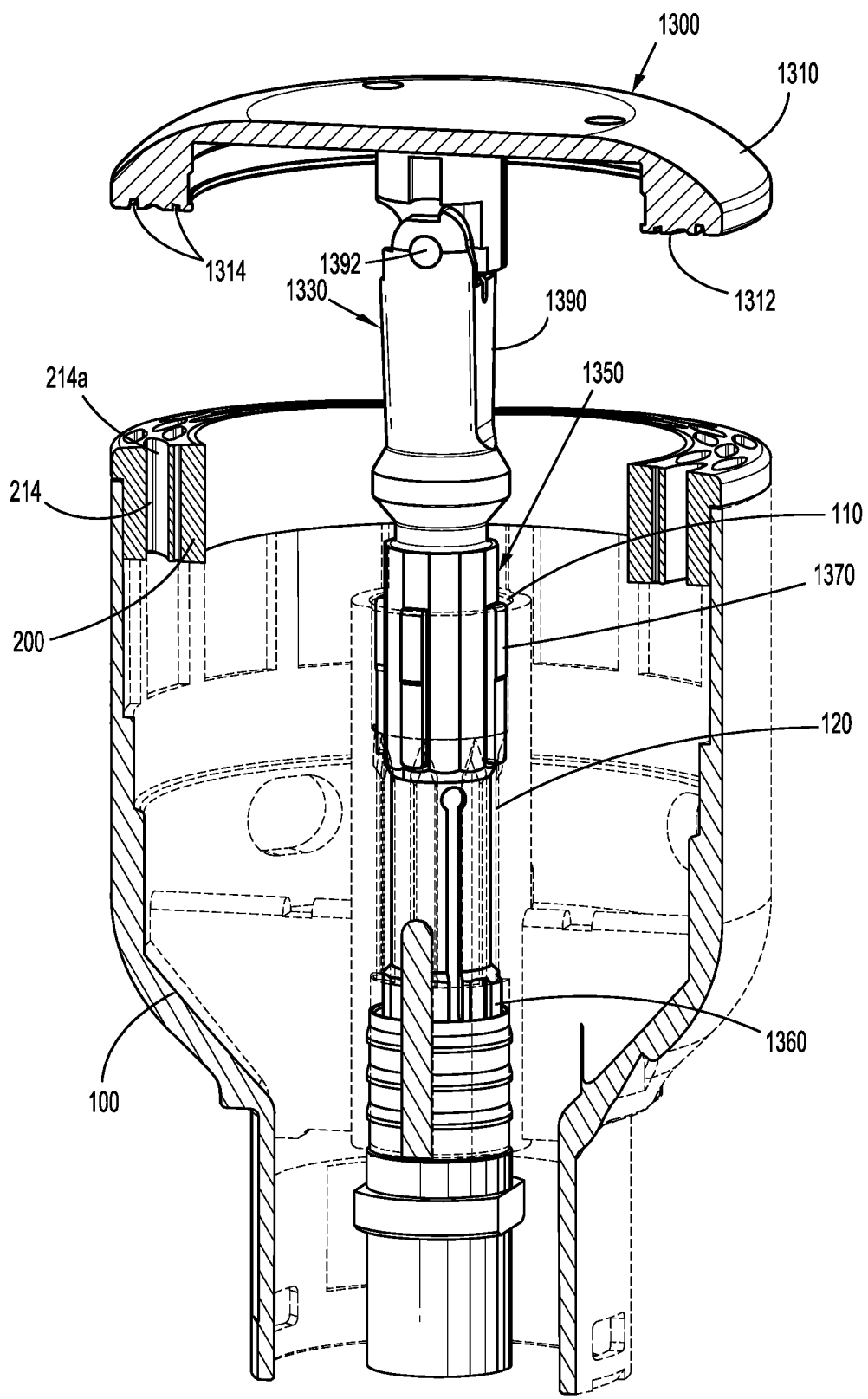
FIG. 16 is a cross-sectional view of the tool assembly of FIG. 16 with each of the tombstone splines received between adjacent alignment splines of the shell.
Figure 17:
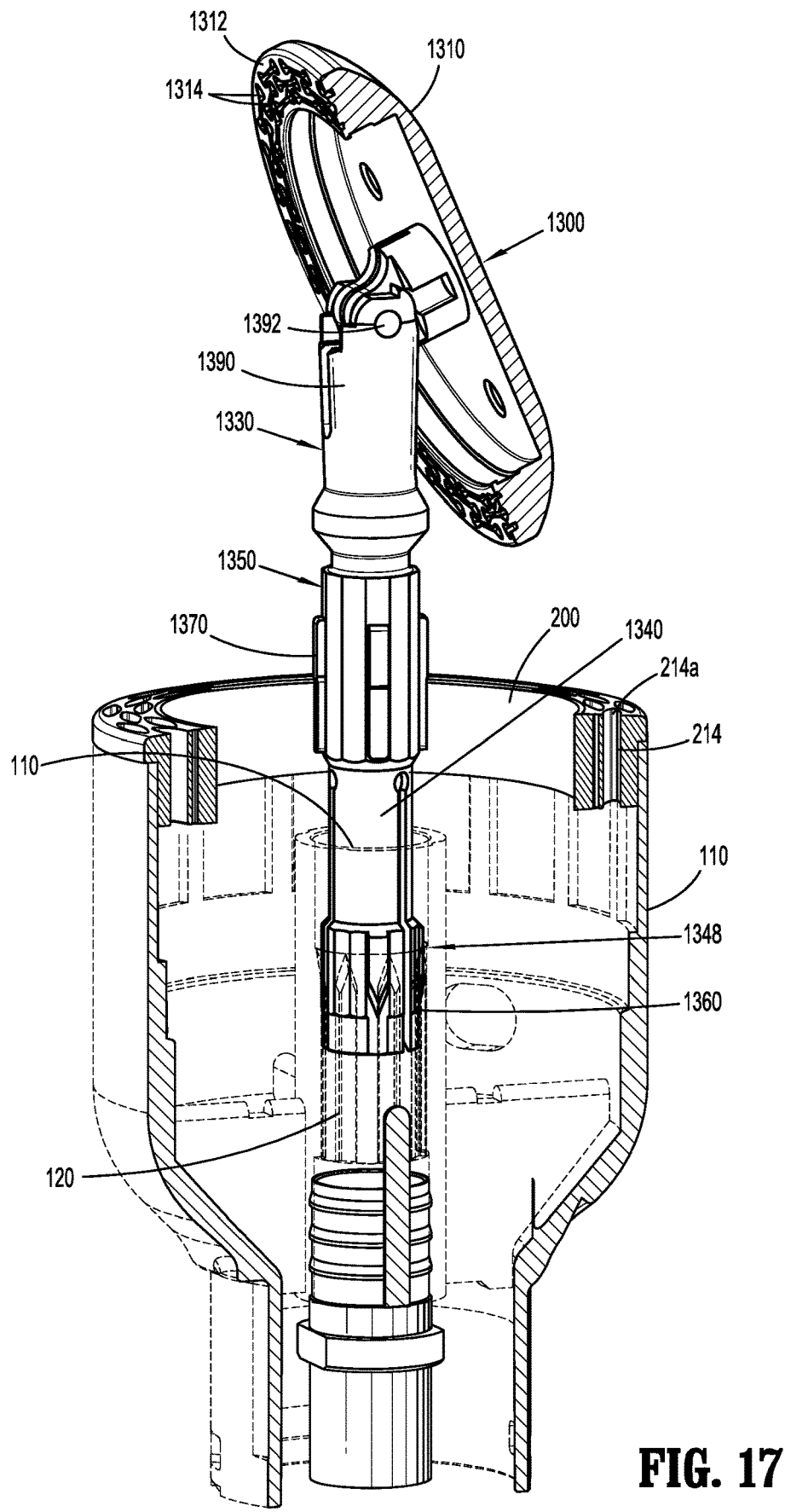
FIG. 17 is a cross-sectional view of an anvil tilted relative to a center rod with each of the locating splines received between adjacent alignment splines of the shell.

With reference to FIGS. 15-17, the locating splines 1360 and tombstone splines 1370 are configured to clock and maintain alignment between the anvil assembly 1300 and the shell 100 as the center rod 1330 passes through the passage 110 of the shell 100. Initially referring to FIG. 15, as the collar 1344 passes through the passage 110, if the locating splines 1360 of the proximal alignment portion 1348 are misaligned with the channels 124, the leading facets 1362 engage the alignment splines 120 of the shell 100 to affect rotation of the anvil assembly 1300 about the longitudinal axis A-A in relation to the shell 100 to clock the anvil assembly 1300 with the shell 100. As compared to the anvil assembly 300 detailed above, clocking of the anvil 1310 occurs with the anvil 1310 spaced a greater distance away from the cartridge assembly 200 than when clocking occurs with the anvil assembly 300. Because of the increased spacing, clocking of the anvil assembly 1300 occurs before increased compression forces are applied to the tissue contacting surfaces 210, 1312 to allow for the anvil assembly 1300 to be clocked with less force when compared to anvil assembly 300. This greater distance is approximately the length of the gap "G". In addition, a strain gage (not shown) may be disposed along the center rod 1330 to detect a compression force applied to tissue between the tissue contacting surfaces 210, 1312. By clocking the anvil 1310 relative to the shell 100 before a compression force is applied to tissue, precision of a measurement of the compression force applied to tissue may be increased by reducing forces attributable to the clocking of the anvil 1310 relative to the shell 100.

Referring now to FIG. 16, as the center rod 1330 is drawn through the passage 110 of the shell 100, each of the tombstone splines 1370 enters a respective channel 124 of the shell 100 after the locating splines 1360 also is already disposed within a respective channel 124. The tombstone splines 1370 detect spline clash and/or anvil mismatch in a manner similar to the manner detailed above with respect to tombstone splines 370. After the tombstone splines 1370 are disposed within channels 124, the locating splines 1360 may extend beyond the alignment splines 120 with the tombstone splines 1370 still positioned with in the channels 124 to maintain alignment between the anvil assembly 1300 and the cartridge assembly 200 during fastener formation.

With reference to FIG. 17, the anvil assembly 1300 can be removed from a tissue segment while being rotatably fixed relative to the shell 100. To remove the anvil assembly 1330 from a tissue segment, the anvil 1310 is tilted relative to the center rod 1330. Tilting the anvil 1310 may reduce contact between the anvil 1310 and the tissue segment to facilitate removal of the anvil 1310. The position of the proximal alignment portion 1348 allows for the anvil 1310 to tilt relative to the center rod 1330 while the locating splines 1360 remain positioned in channels 124 to prevent the anvil assembly 1300 from rotating relative to the shell 100 during removal of the anvil 1310 from a tissue segment which may assist in removal of the anvil 1310 from the tissue segment. It is also contemplated that when the anvil 1310 is tilted relative to the center rod 1330 that a buttress (not shown) can be detached from the tissue contacting surface 1312 of the anvil 1310 while the anvil assembly 1300 is rotatably fixed relative to the shell 100.

As described herein, the circular stapling device is a manually actuated stapling device; however it is contemplated that the shell 100 and the anvil assembly 300 can be used with a powered stapling device, such as an instrument having a motor or being attachable to some power source. For a detailed description of an exemplary powered stapling device reference can be made to U.S. Pat. Nos. 8,806,973 and 9,055,943, the entire contents of which are hereby incorporated by reference.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A tool assembly comprising:
   a cartridge assembly;
   a shell housing the cartridge assembly and defining a passage, the shell including a plurality of alignment splines disposed within the passage, adjacent alignment splines of the plurality of alignment splines defining channels therebetween; and
   an anvil assembly including an anvil and a center rod extending from the anvil, the center rod defining a longitudinal axis and including:
   a first spline including a first leading facet and a trailing end, the first leading facet positioned on the center rod to engage at least one of the plurality of alignment splines to clock the anvil assembly with the cartridge assembly; and
   a plurality of second splines radially spaced apart about the longitudinal axis and positioned distally of the first spline along the longitudinal axis, each of the plurality of second splines including a leading end defining a plane that is substantially orthogonal to the longitudinal axis, the leading end positioned on the center rod to crash with a respective one of the plurality of alignment splines when the anvil assembly is misaligned with the cartridge assembly.

2. The tool assembly according to claim 1, wherein each of the channels is sized to receive at least one of the first or second splines to rotatably fix the anvil assembly relative to the shell.

3. The tool assembly according to claim 1, wherein the first spline includes a second leading facet forming a wedge with the first leading facet, the first and second leading facets meeting at a facet edge.

4. The tool assembly according to claim 3, wherein the facet edge is disposed along a centerline of a body of the first spline.

5. The tool assembly according to claim 1, wherein the first spline is configured to effect rotation of the anvil assembly in a single radial direction as the center rod is retracted through the passage.

6. The tool assembly according to claim 5, wherein the first spline has a body, a first side, a second side, the first leading facet, and a trailing end, the first leading facet extending between the first side and the second side.

7. The tool assembly according to claim 6, wherein the first side forms a leading edge with the first leading facet and the second side forms a trailing edge with the first leading facet.

8. The tool assembly according to claim 7, wherein the leading edge is positioned proximal of the trailing edge.

9. The tool assembly according to claim 5, wherein the single radial direction is counter-clockwise.

10. The tool assembly according to claim 1, wherein the anvil assembly includes a plurality of first splines radially spaced apart about the longitudinal axis.

11. The tool assembly according to claim 1, wherein the center rod includes a first alignment portion and a second alignment portion spaced apart from one another and defining a gap therebetween, the first spline disposed on the first alignment portion and the plurality of second splines disposed about the second alignment portion.

12. The tool assembly according to claim 11, wherein the first spline is radially aligned with a respective one of the second splines.

13. The tool assembly according to claim 11, wherein the anvil is tiltable relative to the center rod between an orthogonal position and a fully tilted position, the gap is sized such that the first spline is disposable within one of the channels of the shell when the anvil is in the fully tilted position.

14. The tool assembly according to claim 11, wherein the gap is in a range of about 0.25 inches to about 0.75 inches.

15. A circular stapling device comprising:
   a handle;
   an elongate body extending from the handle; and
   a tool assembly supported by the elongate body, the tool assembly including:
   a cartridge assembly;
   a shell housing the cartridge assembly and defining a passage, the shell including a plurality of alignment splines disposed within the passage, adjacent alignment splines of the plurality of alignment splines defining channels therebetween; and
   an anvil assembly including an anvil and a center rod extending from the anvil, the center rod defining a longitudinal rod axis and including:
   a first spline including a first leading facet and a trailing end, the first leading facet positioned on the center rod to engage at least one of the plurality of alignment splines to clock the anvil assembly with the cartridge assembly; and
   a plurality of second splines radially spaced apart about the rod axis and positioned distally of the first spline along the longitudinal axis, each of the plurality of second splines including a leading end defining a plane that is substantially orthogonal to the rod axis, the leading end positioned on the center rod to crash with a respective one of the plurality of alignment splines when the anvil assembly is misaligned with the cartridge assembly.

16. The circular stapling device according to claim 15, wherein the elongate body includes an anvil retainer and the center rod includes fingers extending from the alignment portion away from the anvil, the fingers configured to releasably receive the anvil retainer, the anvil retainer configured to draw the center rod through the passage of the shell to approximate the anvil with the cartridge assembly.

17. The circular stapling device according to claim 16, wherein the fingers are sized to pass through and rotate within the passage.

18. The circular stapling device according to claim 16, wherein a proximal portion of the fingers form a collar, the center rod including a first alignment portion adjacent the collar and a second alignment portion, the fingers extending proximally from the second alignment portion, the first spline disposed on the first alignment portion and the plurality of second splines disposed about the second alignment portion.

19. The circular stapling device according to claim 18, wherein the first and second alignment portions define a gap therebetween.

20. A method of aligning an anvil assembly with a cartridge assembly of a circular stapling device, the method comprising:

drawing a center rod of the anvil assembly through a passage of a shell until a first spline disposed on the center rod engages an alignment mechanism of the shell, wherein the shell houses the cartridge assembly;

clocking the anvil assembly with the shell by continuing to draw the center rod through the passage such that the first spline cooperates with the alignment mechanism to rotate the anvil assembly about a longitudinal rod axis defined by the center rod; and approximating the anvil assembly relative to the cartridge assembly by continuing to draw the center rod through the passage such that a plurality of second splines of the center rod radially spaced apart about the longitudinal axis, disposed distal to the first spline along the longitudinal axis, cooperate with the alignment mechanism to rotatably secure the anvil assembly relative to the shell.

21. The method according to claim 20, wherein clocking the anvil assembly with the shell includes engaging a first alignment spline of the alignment mechanism with the first spline to affect rotation of the anvil assembly in a known first direction about the rod axis.

* * * * *